United States Patent [19]

Knippscheer

[11] Patent Number: 5,053,025

[45] Date of Patent: Oct. 1, 1991

[54] METHOD AND APPARATUS FOR EXTRACTING FLUID

[75] Inventor: Hermann Knippscheer, Baldwin, N.Y.

[73] Assignee: Cryo-Cell International, Inc., Baldwin, N.Y.

[21] Appl. No.: 577,269

[22] Filed: Sep. 4, 1990

[51] Int. Cl.$^5$ ............................................. A61B 5/00
[52] U.S. Cl. ...................................... 604/317; 494/42; 128/760
[58] Field of Search ............... 604/317; 494/37, 42–43, 494/84–85; 57/76; 128/760

[56] References Cited

U.S. PATENT DOCUMENTS 4,386,613 6/1983 Locsei .................................. 128/760
4,389,207 6/1983 Bacehowski et al. ................. 494/42

*Primary Examiner*—Randall L. Green
*Assistant Examiner*—G. Gualtieri
*Attorney, Agent, or Firm*—R. Neil Sudol; Henry D. Coleman

[57] ABSTRACT

An apparatus for extracting blood fluids from a placenta and umbilical cord comprises a frame assembly, a rotary carriage mounted to the frame assembly for rotation about a vertical axis, a drive operatively connected to the carriage for rotating the carriage about the axis, and a support for holding the placenta and the umbilical cord. A connector pivotably connects the support to the carriage to enable a pivoting of the support about a rotating horizontal axis during rotating of the carriage by the drive, while a collector is attached to the support for enabling a collection of fluid flowing from the placenta and the umbilical cord during operation of the drive. A fluid delivery system is provided for automatically supplying an anticoagulant to extracted blood fluid.

42 Claims, 4 Drawing Sheets

METHOD AND APPARATUS FOR EXTRACTING FLUID

BACKGROUND OF THE INVENTION

This invention relates to a method and apparatus for extracting fluid. More particularly, this invention relates to a method and apparatus for extracting blood from an umbilical cord and placenta.

In many instances, the umbilical cord, like the placenta, is discarded after birth. However, it has been discovered that at least certain constituents of the umbilical cord may have a special usefulness. In a recent advance in the treatment of bone marrow defects in infants, physicians used the blood cells from the umbilical cord of an infant to aid in the regeneration of the stem cells in an older sibling. The blood was separated from the umbilical cord, subsequently frozen, and stored for seven months prior to infusion. Upon thawing, the cells were intravenously infused into the body of the recipient youngster. This technique provides several advantages over conventional marrow transplantation. Using the cord blood in this instance enabled transplant as soon as a compatible sibling was born, while candidates for marrow transplant generally must wait until the newborn is at least six months old. In addition, the procedure eliminates for the donor the pain of marrow extraction.

The use of umbilical cord blood for allogeneic and hematopoietic reconstitution in siblings has been since used in a number of cases. Clearly, umbilical cord blood represents a vast natural resource for medical, research and even identification purposes.

The amount of blood in the umbilical cord represents but a portion of the blood of an infant which is conventionally discarded at birth. The other portion of that disgarded blood resides in the placenta.

OBJECTS OF THE INVENTION

An object of the present invention is to provide a method and an associated apparatus for removing an infant's blood from its umbilical cord and placenta after severance of the umbilical cord from the infant.

Another object of the present invention is to provide such a method and apparatus which is fast and efficient.

Another, more particular, object of the present invention is to provide such a method and apparatus wherein sterility is maintained and contamination avoided.

A further particular object of the present invention is to provide such a method and apparatus wherein an anticoagulant is automatically mixed in with the blood from the placenta and umbilical cord.

Another, more general object of the present invention is to provide a method and apparatus for removing fluid from a fluid-containing member, particularly, an elongate fluid-containing member.

Yet another general object of the present invention is to provide a method and apparatus for subjecting an object or body to rotary motion.

SUMMARY OF THE INVENTION

An apparatus for extracting blood fluids from a placenta and umbilical cord comprises, in accordance with the present invention, a frame assembly, a rotary carriage mounted to the frame assembly for rotation about a vertical axis, a drive operatively connected to the carriage for rotating the carriage about the axis, and a support for holding the placenta and the umbilical cord. A connector pivotably connects the support to the carriage to enable a pivoting of the support about a rotating horizontal axis during rotating of the carriage by the drive, while a collector is attached to the support for enabling a collection of fluid flowing from the placenta and the umbilical cord during operation of the drive.

Pursuant to a feature of the present invention, the support includes an elongate tubular member for receiving the umbilical cord. In addition, the support includes a hollow body member connected to the tubular member at one end thereof for receiving the placenta. Preferably, a pressure applying device is mounted to the support for pressing the placenta into the body member.

Pursuant to another feature of the present invention, the pressure applying device includes an inflatable balloon component. Preferably, the pressure applying device further includes a pressurizing device operatively connected to the balloon component for automatically inflating same.

Pursuant to an additional feature of the present invention, a supply is operatively connected to the support for supplying an anticoagulant to fluid flowing from the placenta and the umbilical cord into the collector. The supply includes a storage tank for storing a supply of the anticoagulant and a delivery system for delivering an amount of the anticoagulant to fluid flowing from the placenta and the umbilical cord into the collector. Preferably, the delivery system includes a metering device for measuring out a predetermined aliquot of the anticoagulant and further includes a pump for pumping the anticoagulant from the storage tank. In one embodiment of the invention, the storage tank is disposed on the support. In an alternative embodiment, the storage tank is disposed on the frame assembly and the delivery system includes a conduit extending through the pivoting connector.

Pursuant to a further feature of the present invention, a cleaning mechanism is operatively connected to the support for enabling a cleaning thereof. Preferably, the cleaning mechanism dispenses a cleaning and/or disinfectant fluid into a chamber in the support which receives the placenta.

In a first particular embodiment of the invention, the cleaning mechanism includes a fluid distribution system extending from the frame assembly, through the carriage and the connector, and into the support. Preferably, the support includes a pipe receiving the umbilical cord and the cleaning mechanism includes a conduit and openings such as nozzles for dispensing a cleaning fluid into the pipe.

In a second particular embodiment of the present invention, the support includes a removable lid assembly, a cleaning device being removably mountable to the support for cleaning it. The lid assembly is preferably connected to the support via a telescoping member.

Pursuant to yet another feature of the present invention, the collector includes a connector for releasably securing a receptacle to the support at a location proximate to a free end of the umbilical cord. The receptacle takes the form of a bag or, more preferably, a vial or ampule.

The above-described apparatus for extracting blood from a placenta and umbilical cord may be useful in other situations for removing fluid from a fluid-containing member. Such an apparatus thus comprises a frame assembly, a rotary carriage mounted to the frame assembly for rotation about a vertical axis, a drive operatively connected to the carriage for rotating the carriage about the axis, and a support for holding the fluid-containing member in a predetermined configuration. A connector pivotably connects the support to the carriage to enable a pivoting of the support about a rotating horizontal axis during rotating of the carriage by the drive, while a collector is attached to the support for enabling a collection of fluid flowing from the fluid-containing member during operation of the drive.

A method for extracting blood from a placenta and umbilical cord comprising, in accordance with the present invention, the steps of (a) disposing the placenta and the umbilical cord on a support, with the umbilical cord in a vertical configuration, (b) rotating the support, together with the placenta and the umbilical cord, about a vertical axis, (c) supporting the umbilical cord so that it maintains a substantially linear configuration during the step of rotating, (d) pivoting the support about a rotating horizontal axis during the step of rotating, and (e) collecting fluid flowing from the placenta and the umbilical cord during the step of rotating.

Where the support includes an elongate tubular member, the step of disposing includes the step of inserting the umbilical cord through an opening at an upper end of the tubular member. The placenta is then inserted into a hollow, preferably conical, receptacle.

Pursuant to another feature of the present invention, the method also includes the step of pressing the placenta into the conical receptacle. Preferably, the step of pressing includes the step of inflating a balloon member to press the placenta into the conical receptacle.

Pursuant to a further feature of the present invention, an anticoagulant is supplied to fluid flowing from the placenta and the umbilical cord during the step of rotating. Preferably, a predetermined aliquot of the anticoagulant is measured out and pumped from a storage tank to a collector.

In accordance with a general conceptualization of the present invention, a device for subjecting a body to a rotary motion comprises a frame assembly and a rotary carriage mounted to the frame assembly for rotation about an axis, the carriage including a receptacle portion defining a chamber for receiving the body, the carriage further including a cover member removably mounted to the receptacle portion. A drive is operatively connected to the carriage for rotating same about the axis, while a pressure exerting device is provided on the cover member for engaging the body upon placement of the body into the chamber and for maintaining the body in a predetermined position in the chamber during operation of the drive.

Preferably, the pressure exerting device includes an inflatable balloon component. The pressure exerting device further includes a pressurizing device operatively connected to the balloon component for automatically inflating the balloon.

Pursuant to another feature of the present invention, the cover member is movably mounted to the receptacle portion, for example, via a telescoping arm. A fluid storage tank is mounted to the cover member, while a fluid delivery system is provided for delivering fluid from the storage tank to an area communicating with the chamber. A collector is attached to the carriage for enabling a collection of fluid flowing from the body during operation of the drive.

DETAILED DESCRIPTION

Figure 1:
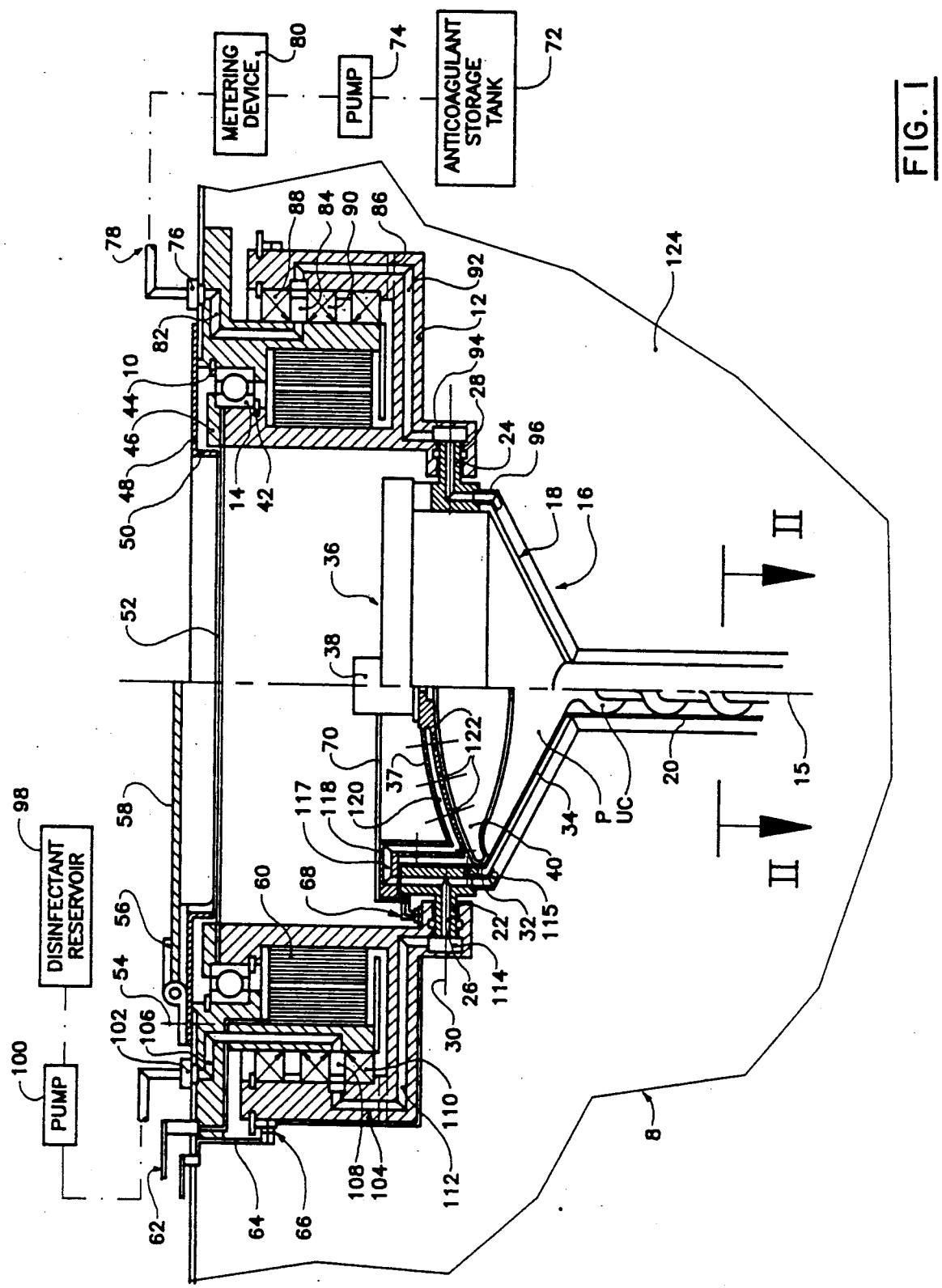
FIG. 1 is a vertical cross-sectional view of an apparatus for extracting fluid from a placenta and umbilical cord, in accordance with the present invention.

As illustrated in FIG. 1, an apparatus 8 for extracting blood from a placenta P and an umbilical cord UC includes a stationary frame 10 and a carriage or carrier 12 mounted to frame 10 via an annular self-maintaining bearing 14, whereby carrier 12 is rotatable about a vertical axis 15. A support member 16 including a receptacle portion 18 and an elongate hollow pipe 20 depending therefrom is pivotably attached to rotary carrier 12 via a pair of pivot pins 22 and 24. Pins 22 and 24 are seated in respective recesses or bores 26 and 28 in a lower end portion of the carrier, whereby support member 16 is enabled to swing about a rotating horizontal axis 30 during turning of carrier 12 about vertical axis 15.

Receptacle portion 18 of support member 16 includes a cylindrical wall 32 and a conical wall 34 integral therewith. Support member 16 also comprises a cover member 36 removably mountable to receptacle portion 18. Attached to an outer side of a dome-shaped section 37 of cover member 36 is a compressor 38 in turn communicating with a balloon 40 disposed inside receptacle portion 18. Upon disposition of umbilical cord UC into pipe 20 and placenta P into receptacle portion 18, and upon the closure of cover member 36, balloon 40 is inflated by compressor 38 to press placenta P against conical wall 34.

Annular bearing 14 and rotary carrier 12 are maintained inside frame 10 by a pair of split rings 42 and 44 and a removable cover ring 46. In addition, a removable annular rim member 48 with an inwardly and downwardly turned lip 50 is disposed about an opening 52 defined by stationary frame 10. Rim member 48 is secured to frame 10 via schematically represented bolts 54 which also fasten a hinge 56 of a door 58.

Electrical windings of a motor 60 for driving rotary carrier 12 relative to frame 10 are disposed between frame 10 and rotary carrier 12. The windings are fed with electrical power via an electrical conduit 62 extending in part through frame 10.

Electrical power and possibly also control signals for compressor 38 are carried thereto via an electrical transmission line 64 including a first slip-ring assembly 66 for enabling power transfer between frame 10 and carrier 12 and a second slip-ring assembly 68 for enabling power transfer from carrier 12 to support member 16. A terminal portion of the electrical transmission line 64 takes the form of a conduit 70 extending to compressor 38.

A liquid anticoagulant from a storage tank 72 is fed by a pump 74 to an inlet 76 of an anticoagulant delivery system 78. Between pump 74 and inlet 76 is a metering device 80 for measuring out a predetermined aliquot of anticoagulant during operation of the rotary drive motor 60.

Liquid anticoagulant flows from inlet 76 through a channel 82 in stationary frame 10 to a first annular chamber 84 defined between frame 10 and an outer cylindrical flange 86 of rotary carrier 16 by a pair of sealing rings 88 and 90 fixed, for example, to an inner surface of flange 86. From annular chamber 84, the anticoagulant flows through a passageway 92 in carrier 16 to an enlargement 94 of the passageway at bore 28. That enlargement 94 communicates with a conduit 96 extending through pin 24 and alongside an outer surface of conical wall 34 and an outer surface of pipe 20.

Figure 3:
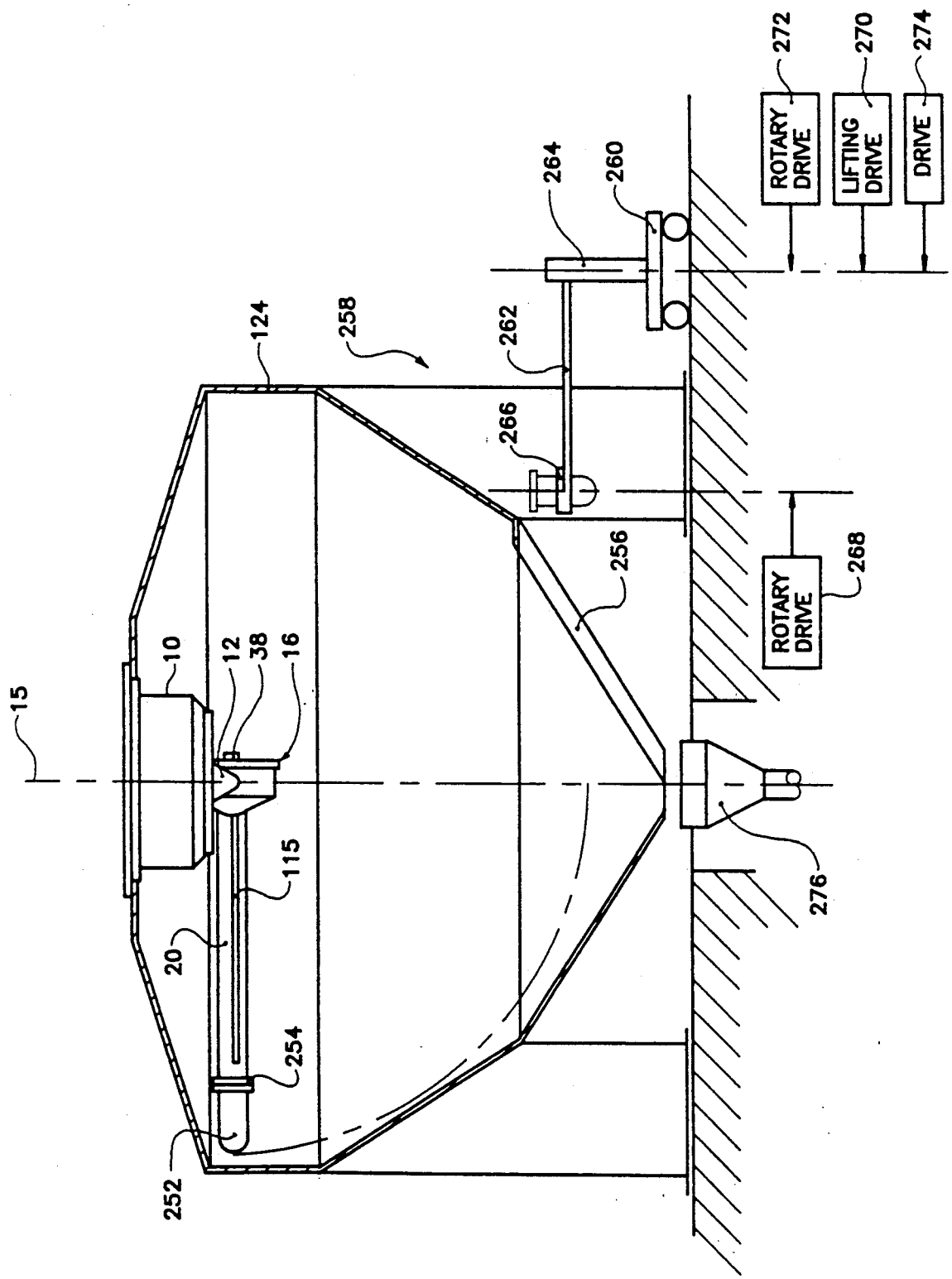
FIG. 3 is a vertical cross-sectional view, on a reduced scale, of the apparatus of FIG. 1, showing the apparatus disposed in a housing and a schematically illustrated vial handling device.

Upon a rotation of carrier 12 and support member 16 about vertical axis 15 and a consequent tilting of support member 16 about horizontal axis 30, pump 74 and metering device 80 are activated (e.g., by a non-illustrated programmed controller or microprocessor) to deliver a predetermined amount of anticoagulant to blood flowing from placenta P and umbilical cord UC into a receptacle, e.g., a vial or ampule, at the free end of pipe 20 (see vial 252 in FIG. 3).

Upon termination of a blood extracting operation, drive motor 60 is de-energized and carrier 12 and support member 16 stop rotating. The blood-collecting vial at the free (lower) end of pipe 20 is detached from the pipe and processed for storage and transport. In addition, compressor 38 is de-energized or reversed to permit the contraction or deflating of balloon 40. Cover member 36 is then removed from the upper end of receptacle portion 18 of support member 16. Placenta P and umbilical cord UC are withdrawn from receptacle portion 18 and pipe 20 and processed for further use.

Upon the removal of placenta P and umbilical cord UC from the apparatus, cover member 36 is replaced for a subsequent cleaning operation. A liquid disinfectant is conveyed from a storage reservoir 98 by a pump 100 to an inlet 102 of a cleaning fluid delivery system 104. Inlet 102 is connected to a channel 106 in stationary frame 10. That channel extends to an annular chamber 108 defined between frame 10 and outer flange 86 by sealing rings 90 and 110. The liquid disinfectant or cleaning fluid flows from chamber 108 through a passageway 112 in carrier 12 to an enlargement 114 at bore 26. Enlargement 114 communicates with a conduit 115 extending through pin 22 and down along an outer surface of conical wall 34 and an outer surface of pipe 20. Conduit 115 communicates with pipe 20 via a series of apertures or nozzle openings 116 (see FIG. 2).

Another conduit 117 extends from pin 22 through a generally L-shaped arm 118 which forms a part of cover member 36. Conduit 117 communicates with a fluid distribution chamber 120 in dome-shaped section 37 of cover member 36. On an inner side dome-shaped section 37 is provided with an array of nozzle openings 122 for spraying the disinfectant into a placenta-receiving chamber defined by cylindrical wall 32, conical wall 34 and cover member 36. During the cleaning operation, balloon 40 is in a deflated state. In addition, motor 60 may be energized to rotate carrier 12 and support member 16. This is particularly effective to clean an inner surface of a housing 124 in which the blood extraction apparatus is disposed. However, it is to be noted that support member 16 is effectively disinfected and sanitized by the cleaning fluid delivery system 104 without operation of motor 60.

To extract infantile blood from placenta P and umbilical cord UC, door 58 is swung about hinge 56 into an opened orientation. Cover member 36 is then removed from receptacle portion 18 of support member 16. Placenta P and umbilical cord UC are lowered into the support member so that umbilical cord UC slides into pipe 20 and placenta P is deposited on conical wall 34. Cover member 36 is then replaced and door 58 closed. At that juncture, compressor 38 is activated to inflate balloon 40. Upon the inflation of balloon 40, motor 60 is energized to begin a spinning or centrifuging operation. Upon the attainment of a preset angular velocity, support member 16 begins to swing about rotating horizontal axis 30. The collector vial or ampule at the end of pipe 20 concomitantly swings outwardly into a configuration aligned essentially with pipe 20. Blood flows from placenta P and umbilical cord UC under the pressure exerted by balloon 40 and compressor 38 and in response to the spinning motion of carrier 12 and support member 16.

Figure 2:
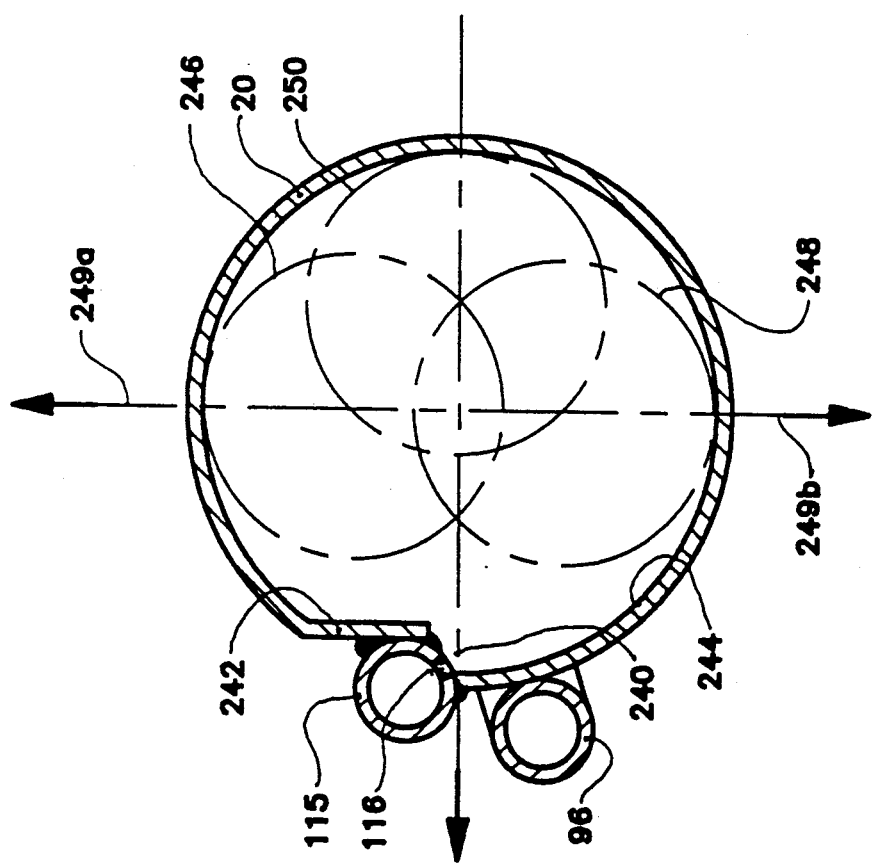
FIG. 2 is a cross-sectional view taken along line II—II in FIG. 1.

As shown in FIG. 2, pipe 20 is provided along a portion of its length with a slot 240 and a planar land strip 242. Conduit 115 is connected to pipe 20 along slot 240 and strip 242. Apertures or nozzle openings 116 are aligned with slot 240 so that disinfectant or cleaning fluid is ejected from nozzle openings 116 and slot 240 in a tangential direction along an inner surface 244 of pipe 20.

FIG. 2 also shows conduit 96 on the same side of pipe 20 as conduit 115. This is the case if conduit 96 is twisted in a helical manner about pipe 20.

Dot-dash circles 246 and 248 in FIG. 2 indicate shifted positions of umbilical cord UC in pipe 20 during an initial phase of a rotation or centrifuging operation. The initial shifted position of umbilical cord depends on the direction 249a or 249b in which support member 16 rotates with respect to carrier 12. Upon a swinging of support member 16 so that pipe 20 assumes horizontal orientation, as illustrated in FIG. 3, umbilical cord UC shifts into a position in pipe 20 opposite conduit 115 and slot 240, as indicated by dot-dash circle 250.

FIG. 3 shows housing 124 in its entirety, as well as a pivoted operational orientation of support member 16 and pipe 20. A vial or ampule 252 for collecting extracted blood fluids is shown attached to a fitting 254 at a free end of pipe 20. Housing 124 is provided in a lower portion with an opening 256 for enabling insertion and removal of vial 252 from pipe 20. The insertion and removal, or attachment and detachment, of vial 252 may be implemented automatically by a schematically depicted loading mechanism 258 including a trolley car 260, an arm 262 rotatably and shiftably mounted to the car via a coupling 264, and a vial holder 266. Vial holder 266 is operatively connected to a rotary drive 268 for rotating vial 252 about a vertical axis to screw the vial onto fitting 254. In addition, coupling 264 is operatively linked to a lifting drive 270 and a rotary drive 272 to facilitate loading and unloading of vial 252 with respect to holder 266 and fitting 254. Finally a linear drive 274 is operatively connected to trolley car 260 for translating the car back and forth with respect to opening 256.

FIG. 3 also depicts a drain 276 for receiving effluent cleaning fluid during a disinfecting or sanitizing operation as described above with reference to cleaning fluid delivery system 104.

Figure 4:
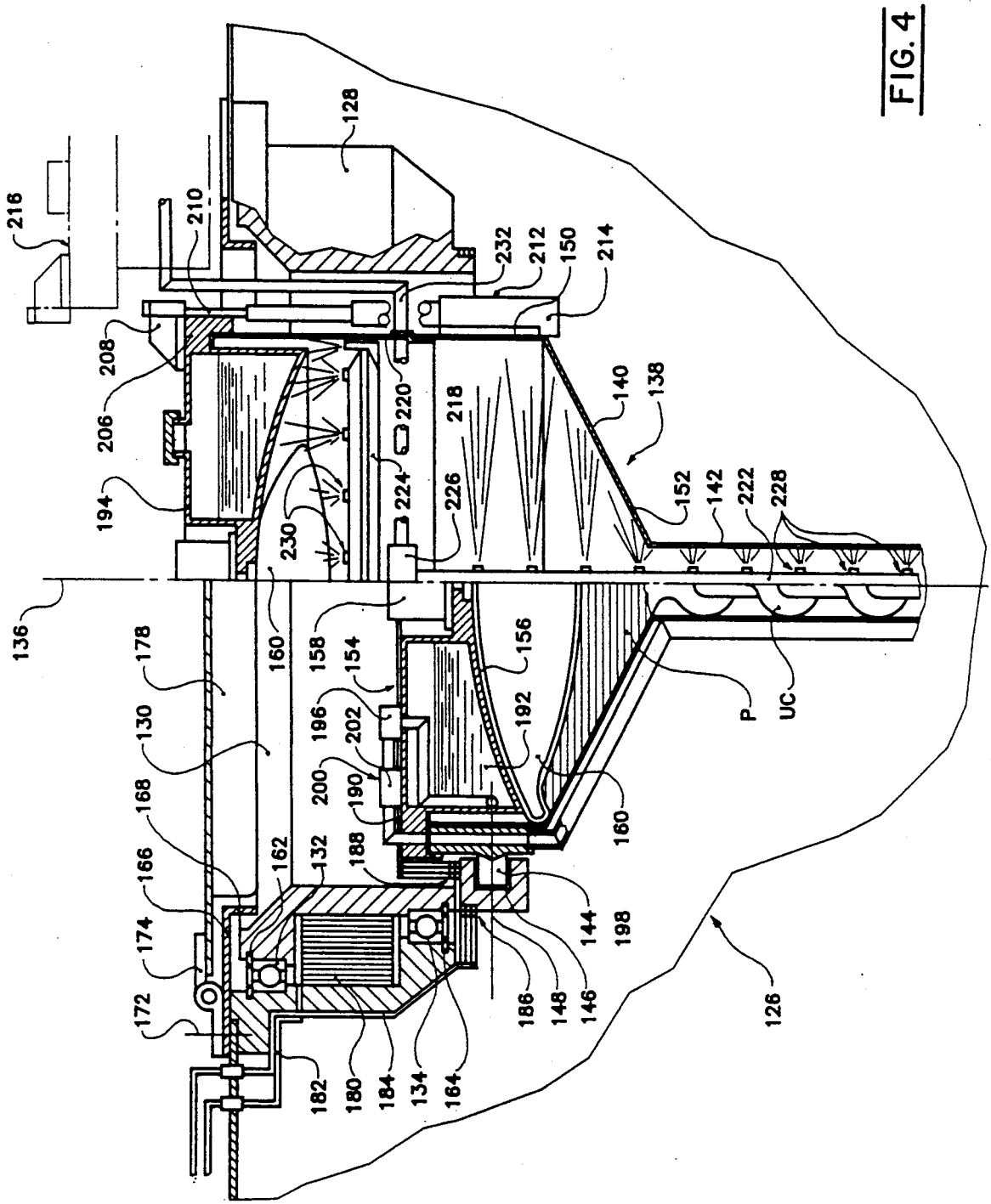
FIG. 4 is a vertical cross-sectional view of another apparatus for extracting fluid from a placenta and umbilical cord, in accordance with the present invention, showing both an operating configuration and a cleaning configuration of the apparatus.

FIG. 4 illustrates, in two operating states, another apparatus 126 for extracting blood from placenta P and umbilical cord UC. The left side of the drawing illustrates a pressure applying operation, while the right side depicts a cleaning operation.

As illustrated in FIG. 4, apparatus 126 comprises a stationary frame 128 and a carriage or carrier 130 mounted to frame 128 via a pair of annular self-maintaining bearings 132 and 134, whereby carrier 130 is rotatable about a vertical axis 136. A support member 138 including a receptacle portion 140 and an elongate hollow pipe 142 depending therefrom is pivotably attached to rotary carrier 130 via a pair of pivot pins 144 (only one illustrated). Pins 144 are seated in respective recesses or bores 146 in a lower end portion of the carrier, whereby support member 138 is enabled to swing about a rotating horizontal axis 148 during turning of carrier 130 about vertical axis 136.

Receptacle portion 140 of support member 138 includes a cylindrical wall 150 and a conical wall 152 integal therewith. Support member 138 also comprises a cover member 154 removably mountable to receptacle portion 140. Attached to an outer side of a dome-shaped section 156 of cover member 154 is a compressor 158 in turn communicating with a balloon 160 disposed inside receptacle portion 140. Upon disposition of umbilical cord UC into pipe 142 and placenta P into receptacle portion 140, and upon the closure of cover member 154, balloon 160 is inflated by compressor 158 to press placenta P against conical wall 152, as depicted on the left-had side of FIG. 4. The right hand side of that drawing figure shows balloon 160 in a deflated state 161.

Annular bearings 132 and 134 and rotary carrier 130 are maintained inside frame 128 by a pair of split rings 162 and 164. In addition, a removable annular rim member 166 with an inwardly and downwardly turned lip 168 is disposed about an opening defined by the inner diamter of carrier 130. Rim member 166 is secured to frame 128 via schematically represented bolts 172 which also fasten a hinge 174 of a door 178.

Electrical windings of a motor 180 for driving rotary carrier 130 relative to frame 128 are disposed between frame 128 and rotary carrier 130. The windings are fed with electrical power via an electrical conduit 182 extending in part through frame 128.

Electrical power and possibly also control signals for compressor 158 are carried thereto via an electrical transmission line 184 including a first slip-ring assembly 186 for enabling power transfer between frame 128 and carrier 130 and a second slip-ring assembly 188 for enabling power transfer from carrier 130 to support member 138. A terminal portion of the electrical transmission line 184 takes the form of a conduit 190 extending to compressor 158.

A liquid anticoagulant 192 from an annular storage tank 194 incorporated into cover member 154 is fed by a pump 196 through a conduit or tube 198 an anticoagulant delivery system 200. At an output side of pump 196 is a metering device 202 for measuring out a predetermined aliquot of anticoagulant during operation of the rotary drive motor 180.

As shown in FIG. 4, cover member 154 includes dome-shaped wall 156 which serves as a pressure plate for balloon 160. Cover member 154 further includes an annular flange 206 which is connected via a bracket assembly 208 to an innermost tubular member 210 of a telescoping connector 212. An outermost tubular member or casing 214 of telescoping connector 212 is fastened to an outer side of cylindrical wall 150. Telescoping connector 212 attaches cover member 154 to receptacle portion 140 to enable a vertical removal of the cover member and a pivoting of the cover member from a position vertically aligned with receptacle portion 140 to a side position 216 indicated in dot-dash lines in FIG. 4.

To operate blood extraction apparatus 126, an operator opens lid or door 178 by pivoting the door about hinge 174. Cover member 154 is lifted from receptacle portion 140 and, at an uppermost extension of telescoping connector 212, swung into side position 216. Placenta P and umbilical cord UC are then inserted into support member 138, as described hereinabove with reference to the embodiment of FIG. 1.

Upon the disposition of placenta P and umbilical cord UC, cover member 154 is replaced, door 178 is closed and compressor 158 is activated to inflate balloon 160. Motor 180 is then energized to rotate carrier 130 and support member 138 about vertical axis 136. During that rotation, support member eventually pivots about rotating horizontal axis 148 so that pipe 142 assumes a horizontal or nearly horizontal orientation (see FIG. 3).

Upon the termination of the blood extraction operation, motor 180 is de-energized. When carrier 130 and support member 138 stops their rotation, a vial 252 (see FIG. 3) with collected blood fluids is removed from the free (lower) end of pipe 142. Compressor 158 is turned off or reversed, deflating balloon 160. Cover member 154 is then removed, as described above. Upon the withdrawal of placenta P and umbilical cord UC from receptacle portion 140 and pipe 142, a cleaning device 218 is lowered into rotary carrier 130, receptacle portion 140 of support member 138 and pipe 142, and cover member is rotated back from side position 216 and lowered onto an upper end of the cleaning device.

Cleaning device 218 specifically includes a cylindrical holder 220, as well as a tubular member 222 and a spray arm 224 rotatably mounted to the cylindrical holder 220 via a rotary coupling or joint 226. Tubular member 222 is provided with a longitudinal array of spraying nozzles 228, while arm 224 is likewise formed with a plurality of spray openings 230. Rotary coupling 226 is connected via a conduit 232 to a source of disinfectant or cleaning fluid (not shown in FIG. 4) via a pump (see FIG. 1). Upon a pressurization of tubular member 222 and arm 224 with cleaning fluid and the consequent spraying of the fluid through nozzles 228 and openings 230, tubular member 222 and arm 224 rotating about vertical axis 136, thereby sanitizing the inside of pipe 142, the outside of balloon 160 and the underside of dome-shaped wall 156, as well as other surfaces of support member 138.

As described above with reference to FIG. 1, anticoagulant 192 from storage tank 194 is supplied by pump 196 and metered by device 202. The anticoagulant is delived through conduit or tube 198 into pipe 142 proximately to a free end thereof, for mixture with blood fluids forced from placenta P and umbilical cord UC during operation of the apparatus 126.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are profferred by way of example to facilitate comprehension of the invention and should not be construed to limit the scope thereof.

What is claimed is:

1. An apparatus for extracting blood fluids from a placenta, comprising:
   a frame assembly;
   a rotary carriage mounted to said frame assembly for rotation about a vertical axis;
   drive means operatively connected to said carriage for rotating same about said axis;
   support means for holding the placenta;
   connector means for pivotably connecting said support means to said carriage to enable a pivoting of said support means about a rotating horizontal axis during rotating of said carriage by said drive means; and
   collector means attached to said support means for enabling a collection of blood fluid flowing from said placenta during operation of said drive means.

2. The apparatus recited in claim 1 wherein an umbilical cord is attached to said placenta, said support means including an elongate tubular member for receiving said umbilical cord.

3. The apparatus recited in claim 2 wherein said support means includes a hollow body member connected to said tubular member at one end thereof.

4. The apparatus recited in claim 3 wherein said body member includes a conical portion joined to a cylindrical portion, said connector means connecting said cylindrical portion to said carriage.

5. The apparatus recited in claim 1, further comprising pressure means mounted at least in part to said support means for pressing said placenta against a portion of said support means.

6. The apparatus recited in claim 5 wherein said pressure means includes an inflatable balloon component.

7. The apparatus recited in claim 6 wherein said pressure means further includes pressurization means operatively connected to said balloon component for automatically inflating same.

8. The apparatus recited in claim 1, further comprising supply means operatively connected to said support means for supplying an anticoagulant to blood fluid flowing into said collector means.

9. The apparatus recited in claim 8 wherein said supply means includes storage means for storing a supply of said anticoagulant and delivery means for delivering an amount of said anticoagulant to blood fluid flowing into said collector means.

10. The apparatus recited in claim 9 wherein said delivery means includes means for measuring out a predetermined aliquot of said anticoagulant.

11. The apparatus recited in claim 9 wherein said delivery means includes pumping means for pumping said anticoagulant from said storage means.

12. The apparatus recited in claim 9 wherein said storage means is disposed on said support means.

13. The apparatus recited in claim 9 wherein said storage means is disposed on said frame assembly and said delivery means includes a conduit extending through said connector means.

14. The apparatus recited in claim 1, further comprising cleaning means operatively connected to said support means for enabling a cleaning thereof.

15. The apparatus recited in claim 14 wherein said cleaning means includes means for dispensing a cleaning fluid into a chamber in said support means which receives said placenta.

16. The apparatus recited in claim 15 wherein said means for dispensing includes a conduit system extending from said frame assembly, through said carriage and said connector means, and into said support means.

17. The apparatus recited in claim 14 wherein an umbilical cord is attached to said placenta, said support means including a pipe receiving said umbilical cord, said cleaning means includes means for dispensing a cleaning fluid into said pipe.

18. The apparatus recited in claim 17 wherein said means for dispensing includes openings in said pipe.

19. The apparatus recited in claim 1 wherein said support means includes a removable lid assembly, further comprising cleaning means removably mountable to said support means for cleaning same.

20. The apparatus recited in claim 19 wherein said lid assembly is connected to said support means via a telescoping member.

21. The apparatus recited in claim 1 wherein said collector means includes connection means for releasably securing a receptacle to said support means.

22. The apparatus recited in claim 21 wherein said receptacle takes the form of a vial or ampule.

23. An apparatus for subjecting an object to a centrifuging operation, comprising:
   a frame assembly;
   a rotary carriage mounted to said frame assembly for rotation about a vertical axis;
   drive means operatively connected to said carriage for rotating same about said axis;
   support means for holding the object; and
   connector means for pivotably connecting said support means to said carriage to enable a pivoting of said support means about a rotating horizontal axis during rotating of said carriage by said drive means.

24. The apparatus recited in claim 23, further comprising collector means attached to said support means for enabling a collection of fluid flowing from said object during operation of said drive means.

25. The apparatus recited in claim 24 wherein said collector means includes connection means for releasably securing a receptacle to said support means.

26. The apparatus recited in claim 25 wherein said receptacle takes the form of a vial or ampule.

27. The apparatus recited in claim 23 wherein said object includes an elongate component and said support means includes an elongate tubular member for receiving said elongate component.

28. An apparatus for subjecting a body to a rotary motion, comprising:
   a frame assembly;
   a rotary carriage mounted to said frame assembly for rotation about an axis, said carriage including a receptacle portion defining a chamber for receiving said body, said carriage further including a cover member removably mounted to said receptacle portion;
   drive means operatively connected to said carriage for rotating same about said axis; and
   pressure means on said cover member for engaging said body upon placement of said body into said chamber and for maintaining said body in a predetermined position in said chamber during operation of said drive means.

29. The apparatus recited in claim 28 wherein said pressure means includes an inflatable balloon component.

30. The apparatus recited in claim 29 wherein said pressure means further includes pressurization means operatively connected to said balloon component for automatically inflating same.

31. The apparatus recited in claim 28, further comprising means for movably coupling said cover member to said receptacle portion.

32. The apparatus recited in claim 31 wherein said means for movably coupling includes a telescoping arm.

33. The apparatus recited in claim 28, further comprising a fluid storage tank mounted to said cover member and means for delivering fluid from said storage tank to an area communicating with said chamber.

34. The apparatus recited in claim 28, further comprising collector means attached to said carriage for enabling a collection of fluid flowing from said body during operation of said drive means.

35. A method for extracting blood from a placenta and umbilical cord, comprising the steps of:
disposing the placenta and the umbilical cord on a support, with the umbilical cord in a vertical configuration;
rotating the support, together with said placenta and said umbilical cord, about a vertical axis;
supporting said umbilical cord so that it maintains a substantially linear configuration during said step of rotating;
pivoting said support about a rotating horizontal axis during said step of rotating; and
collecting fluid flowing from said placenta and said umbilical cord during said step of rotating.

36. The method recited in claim 35 wherein said support includes an elongate tubular member, said step of disposing includes the step of inserting said umbilical cord through an opening at an upper end of said tubular member.

37. The method recited in claim 36 wherein said step of disposing further includes the step of inserting said placenta into a hollow conical receptacle.

38. The method recited in claim 37, further comprising the step of pressing said placenta into said conical receptacle.

39. The method recited in claim 38 wherein said step of pressing includes the step of inflating a balloon member to press said placenta into said conical receptacle.

40. The method recited in claim 35, further comprising the step of supplying an anticoagulant to fluid flowing from said placenta and said umbilical cord during said step of rotating.

41. The method recited in claim 40 wherein said step of supplying includes the step of measuring out a predetermined aliquot of said anticoagulant.

42. The method recited in claim 40 wherein said step of supplying includes the step of pumping said anticoagulant from storage means.

* * * * *